(12) United States Patent
Gebhardt et al.

(10) Patent No.: US 10,130,262 B2
(45) Date of Patent: Nov. 20, 2018

(54) DENTAL CAMERA FOR DETECTING CARIES

(71) Applicant: Dürr Dental AG, Bietigheim-Bissingen (DE)

(72) Inventors: Herbert Gebhardt, Siegelsbach (DE); Peter Lais, Erlingheim (DE); Raimund Maier, Tamm (DE)

(73) Assignee: Dürr Dental AG, Bietigheim-Bissingen (DE)

( * ) Notice: Subject to any disclaimer, the term of this patent is extended or adjusted under 35 U.S.C. 154(b) by 684 days.

(21) Appl. No.: 14/255,112

(22) Filed: Apr. 17, 2014

(65) Prior Publication Data

US 2014/0313299 A1    Oct. 23, 2014

(30) Foreign Application Priority Data

Apr. 18, 2013   (DE) .................. 10 2013 006 636

(51) Int. Cl.

| | |
|---|---|
| *H04N 5/00* | (2011.01) |
| *A61B 5/00* | (2006.01) |
| *H04N 5/225* | (2006.01) |
| *H04N 5/33* | (2006.01) |
| *A61B 1/24* | (2006.01) |

(52) U.S. Cl.
CPC .............. *A61B 5/0088* (2013.01); *A61B 1/24* (2013.01); *H04N 5/2251* (2013.01); *H04N 5/2256* (2013.01); *H04N 5/33* (2013.01); *H04N 2005/2255* (2013.01)

(58) Field of Classification Search
CPC ......... A61C 19/00; A61B 1/0638; A61B 1/24; A61B 5/0088; A61B 1/00186; A61B 1/043; A61B 1/0607; A61B 1/0646; A61B 1/0016; A61B 1/00172; A61B 5/0073;
(Continued)

(56) References Cited

U.S. PATENT DOCUMENTS

| | | |
|---|---|---|
| 8,332,015 B2 | 12/2012 | Ertl |
| 2007/0134615 A1 | 6/2007 | Lovely |

(Continued)

FOREIGN PATENT DOCUMENTS

| | | |
|---|---|---|
| DE | 10 2004 024 494 A1 | 12/2005 |
| DE | 10 2007 046 228 A1 | 4/2009 |

(Continued)

*Primary Examiner* — Frank Huang
(74) *Attorney, Agent, or Firm* — Schroeder Intellectual Property Law Group, LLC

(57) ABSTRACT

A camera head of a dental camera for detecting caries in an interdental space has an illuminating device for illuminating a tooth adjacent to the interdental space, which includes an infrared light source. The camera head further includes optics which have an image plane and an object plane, wherein an image sensor is located in the image plane, and the object plane divides the space into two half spaces, wherein a first half space contains the optics and is located in front of the object plane, and a second half space is located behind the object plane, both as seen from the optics. The illuminating device and the optics are designed and arranged with respect to one another in such a way that the illuminating device is arranged in the first half space and infrared light exiting the illuminating device is aimed in the direction of the second half space.

14 Claims, 7 Drawing Sheets

(58) Field of Classification Search
CPC .......... H04N 7/18; H04N 7/183; G01N 21/71; A61K 6/00; A61K 33/42
See application file for complete search history.

(56) References Cited

U.S. PATENT DOCUMENTS

| | | |
|---|---|---|
| 2008/0082000 A1 | 4/2008 | Thoms |
| 2009/0087811 A1 | 4/2009 | Ertl |
| 2009/0181339 A1* | 7/2009 | Liang ................... A61B 1/0638 433/29 |
| 2010/0279248 A1 | 11/2010 | Mourad et al. |
| 2012/0130254 A1 | 5/2012 | Hackel et al. |
| 2012/0156634 A1* | 6/2012 | Duff, Jr. ............... A61B 1/0016 433/29 |
| 2013/0183633 A1* | 7/2013 | Dillon ................ A61B 1/00048 433/31 |
| 2014/0085449 A1* | 3/2014 | Mandelis ............. A61B 5/0073 348/77 |
| 2014/0093457 A1* | 4/2014 | Nagai ................ A61K 31/6615 424/9.6 |

FOREIGN PATENT DOCUMENTS

| | | |
|---|---|---|
| DE | 10 2009 017 819 A1 | 10/2010 |
| DE | 10 2010 043 796 A1 | 5/2012 |

\* cited by examiner

DENTAL CAMERA FOR DETECTING CARIES

CROSS-REFERENCE TO RELATED APPLICATIONS

The present application claims priority to German Patent Application No. 10 2013 006 636.0 filed Apr. 18, 2013, the contents of which are incorporated herein by reference.

FIELD OF THE INVENTION

The invention relates to a dental camera head for detecting caries in an interdental space and a dental camera having a camera head of this type.

BACKGROUND OF THE INVENTION

Dental cameras are used in dentistry for taking photographs of the mouth, in particular the inside of the mouth and the teeth arranged therein. The representations produced can be displayed on a display device by the treating doctor for the purpose of diagnosis or for discussing treatment options with the patient. A dental camera of this type is disclosed for example in DE 10 2009 017 819 A1.

Dental cameras are furthermore known, which present further diagnostic options over a conventional imaging function, such as caries detection.

Therefore, DE 10 2010 043 796 A1 discloses a dental camera in which a tooth is transilluminated, i.e. has light passed through it, substantially from below in opposition to the viewing direction of camera optics by lateral irradiation with light having a wavelength of 780 nm at the lower gum line. Since healthy tooth enamel is transparent to light of this wavelength, whereas dental caries are not, carious regions of the tooth appear as dark spots in the photographs captured by the camera optics. This known transilluminating dental camera is disadvantageous in that illuminating arms which reach around the tooth on both sides are required to irradiate the light at the lower gum line, and these are sometimes difficult to position. Moreover, differently spaced illuminating arms are required for teeth of varying thicknesses.

DE 10 2004 024 494 A1 discloses a dental camera in which the teeth are illuminated with UV light and it is possible to differentiate between healthy and unhealthy dental tissue by capturing the fluorescent light emitted. However, detecting caries in this way by measuring fluorescent light is not, or not sufficiently, suitable for identifying dental caries in the interdental spaces, in particular between the back teeth. However, dental caries occurs particularly frequently on the approximal surfaces of the back teeth and is otherwise difficult for the dentist to identify visually. Reliable device-aided caries detection is therefore necessary in precisely this area.

SUMMARY OF THE INVENTION

It is therefore an object of the invention to provide a camera head of a dental camera and a dental camera with a camera head of this type, which is easy to handle and is notably suitable for detecting caries in an interdental space.

According to the invention, this may be achieved by a camera head which has an illuminating device which comprises an infrared light source. The camera head furthermore has optics which have an image plane and an object plane, wherein an image sensor is located in the image plane and the object plane divides the space into two half spaces, wherein a first half space contains the optics and is located in front of the object plane as seen from the optics, and a second half space is located behind the object plane as seen from the optics. The illuminating device and the optics are furthermore designed and arranged with respect to one another in such a way that the illuminating device is arranged in the first half space and infrared light exiting the illuminating device is aimed in the direction of the second half space.

The basic idea of the invention is based on establishing a type of backscatter geometry, in which the side from which the tooth is observed is essentially the same as that from which the illumination also takes place, instead of the known scanning geometry, in which a tooth to be examined is illuminated from the one side and observed from the other side. This may be achieved in that infrared light, to which the dental enamel of a tooth is transparent, is essentially aimed in the direction of the half space located behind the object plane from the half space which contains the optics. The important factor here is not that the infrared light also arrives in the rear half space, but rather that the infrared light disperses substantially in the opposite direction to a light entry direction of the optics.

The object plane refers to that plane which is imaged by the optics with a maximum sharpness and in which a tooth to be examined is arranged. With given optics, the axial position of the object plane is determined by the image distance, i.e. by the distance between the optics and the image plane. An image sensor which can also be located outside the camera head is arranged in this image plane.

During use of the dental camera, the camera head is aligned, for example, so that the object plane extends substantially parallel to the occlusal surface of a tooth. The tooth is then illuminated from the occlusal surface by the infrared light. Since the tooth enamel is transparent to the infrared light, this then enters the tooth enamel and is guided in this for example along the approximal surface of the tooth into the gum and absorbed there. On the other hand, the dentine, i.e. the core of the tooth, and regions of the tooth enamel which are affected by caries have a different structure and are not transparent to the infrared light, but scatter this back inter alia in the direction of the optics. The thereby backscattered infrared light is perceived as a bright spot by the image sensor. Since the affected region can only be differentiated from the dentine of the tooth with difficulty using this backscatter geometry, a camera head of this type is particularly suitable for detecting caries in the interdental space, more precisely on the approximal surfaces of the adjacent teeth. This is because, when viewed from above, the tooth enamel of the approximal surface is transparent over the entire height of the tooth, i.e. to the point where the infrared light is absorbed in the jaw area, since the dentine is only located inside the tooth.

The illuminating device can be advantageously designed in such a way that the infrared light exiting the illuminating device has a main emission direction which is parallel to an optical axis of the optics or extends at an angle to the optical axis of the optics which is less than 45°, preferably less than 15°.

With an illuminating device which is designed in this way, it is possible to illuminate the tooth substantially from above, i.e. from the occlusal surface, so that infrared light hits the tooth substantially in the opposite direction to a light entry direction of the optics.

To highlight carious points in the interdental space even more clearly, the optics can have an optical axis and the optics can image an object field, which is located in the object plane and can be directed at the interdental space, on the image sensor, in which case the illuminating device does not illuminate the object field or at least a cohesive sub-region of the object field which contains the optical axis. In particular, the illuminating device can be designed here to illuminate an occlusal surface of a tooth which is adjacent to the interdental space.

If a camera head of this type is aligned during use so that the object field or at least the said sub-region covers the relevant interdental space for caries detection, the infrared light is only directed onto the occlusal surface of a tooth adjacent to the interdental space (or the occlusal surfaces of both adjacent teeth). The illumination according to the invention ensures here that the region of the interdental space captured by the image sensor is itself not directly illuminated. In particular, if the main emission direction of the illuminating device and the optical axis of the optics are parallel to one another, it is generally ensured that infrared light is not aimed directly into the object field.

In this configuration, the tooth enamel of the occlusal surface of the tooth, which is transparent to the infrared light used, acts as a type of light guide and guides the infrared light inside the tooth enamel in the direction of the approximal surface. A region of the tooth enamel which may be affected by caries there then scatters the infrared light back again for the most part in the direction of the optics. The advantage of this method is that the infrared light does not enter the tooth enamel through the outer surfaces of the tooth within the object field. This is because, as it passes through the outer surfaces, a certain proportion of the infrared light is always scattered back and would result in an undesired background signal if the object field or the sub-region of interest were illuminated directly. This mode of operation of the dental camera according to the invention is similar to the dark field illumination known in microscopes, wherein the object field or the sub-region which is relevant for caries detection is however illuminated indirectly by way of the occlusal surface of the tooth adjacent to the interdental space.

For these ideas of the invention, it is irrelevant whether the entire object field imaged onto the image sensor is excluded from illumination and used for detecting caries or whether this only applies to a central sub-region of the object field, which therefore contains the optical axis. If the text below refers simply to "object field", this should be understood to mean "object field or at least a cohesive sub-region thereof, which contains the optical axis".

So that the infrared light can exit the housing of the camera head, the illuminating device will have a light exit window.

The light exit window of the illuminating device can be at a spacing from an entrance window of the optics here, with the spacing preferably being ca. 2 mm to ca. 5 mm, in particular ca. 4 mm.

This spacing corresponds to approximately half a tooth diameter of the molar and premolar back teeth so that, when the camera head is orientated and arranged accordingly above one of these teeth, the object field captures the interdental space and the occlusal surface is illuminated by way of the light exit window. When used for children or in a veterinary application, for example for horses, it is optionally possible to select an appropriately adapted spacing between the entrance window of the optics and the light exit window of the illuminating device.

The light exit window can furthermore extend arcuately, in particularly completely annularly, around an entrance window of the optics.

This enables the camera to be rotated in different rotational orientations about the optical axis of the optics with respect to the dental arch, with it still being possible to ensure illumination of the occlusal surface of the adjacent tooth. The camera head can therefore be used comfortably both for interdental spaces which are located deep inside the mouth and for the interdental spaces which are arranged further forwards on the dental arch. Instead of a continuous arcuate light exit window, it is also possible to arrange individual light exit windows which are arranged along an arc and are each arranged at a suitable spacing from the entrance window of the optics. The illuminating device can furthermore have a plurality of infrared light sources which are each arranged at a different circumferential angle around the entrance window of the optics. These can moreover be individually actuated manually or automatically so that, depending on the orientation of the camera head with respect to the dental arch, the infrared light source which is activated is the one which is then arranged approximately centrally above the appropriate tooth and therefore illuminates this optimally.

It is furthermore possible to arrange a light barrier between the light exit window of the illuminating device and an entrance window of the optics.

This can be for example a strip which is arranged between the light exit window and the entrance window of the optics and prevents the exiting infrared light being directed onto the object field of the optics. A strip of this type can be for example approximately 3 mm high and can preferably extend completely round the entrance window of the optics.

A light barrier of this type can preferably be constructed as a light barrier sleeve which can be connected and released from the camera head without tools.

To this end, the light barrier sleeve can be made from a resilient material and can be latched for example to a latching joint extending around the entrance window of the optics. However, it can also be pushed onto the entire camera head as a type of cap.

The infrared light source should preferably generate infrared light with a medium wavelength which is between ca. 760 nm and 1000 nm, preferably between ca. 820 nm and 890 nm, in particular ca. 850 nm.

An infrared light source of this type can be realised in simple manner by way of an IR LED or an IR laser diode. The infrared light is therefore matched optimally both to the necessary transparency of the tooth enamel in this wavelength range and to the sensitivity of an image sensor used in the dental camera. The infrared light selected is moreover suitable both for use with milk teeth and for use with permanent teeth.

It is particularly advantageous if the illuminating device comprises two infrared light sources which are arranged diametrically opposed in relation to an entrance window of the optics.

This enables both teeth which are adjacent to an interdental space to be illuminated by way of their occlusal surfaces. The infrared light thus hits the interdental space from both approximal surfaces, so that it is possible to identify any caries which may be present on both teeth at the same time. This is advantageous since such a clinical picture of an attack on both approximal surfaces is highly likely. The two diametrically opposed infrared light sources can preferably be actuated independently of one another so that it is possible to switch between two-sided or only one-sided illumination.

It is likewise advantageously possible to provide a further illuminating device which comprises a white light source and illuminates the object field, with the optics being permeable to both visible light and also to infrared light of the infrared light source. This also enables conventional photographs to be taken with visible light in addition to the caries detection, for example by alternate pulses from the infrared light source and the white light source. These photographs can then be shown on a display device, with the carious points on the approximal surfaces being represented for example by way of a false colour overlay.

The camera head can furthermore be constructed as a removable tip which can preferably be releasably connected to a base portion of a dental camera by way of a latching connection. A construction of this type enables only the image sensor and corresponding control electronics to be arranged in the base portion of a dental camera. It is then possible to attach a removable tip which is optimised in each case for different purposes to the base portion for different applications. In the present case, this would be a removable tip for detecting caries on approximal surfaces, which substantially comprises the above-described illuminating device and optics on the camera head.

An object of the invention is therefore also a dental camera for detecting caries in an interdental space, which has a base portion on which an image sensor is arranged, and a camera head described above, which is constructed as a removable tip.

It goes without saying that a dental camera of this type can also be constructed as a standardised dental camera so that, according to another aspect of the invention, a dental camera is provided for detecting caries in an interdental space, wherein the dental camera comprises an illuminating device which comprises an infrared light source. The dental camera furthermore comprises optics which have an image plane and an object plane, with the object plane dividing the space into two half spaces. A first half space here contains the optics and is located in front of the object plane as seen from the optics. A second half space is then located behind the object plane as seen from the optics. According to the invention, the illuminating device and the optics here are designed and arranged with respect to one another in such a way that the illuminating device is arranged in the first half space and infrared light exiting the illuminating device is aimed in the direction of the second half space.

A dental camera of this type can also have the advantageous features described for the camera head.

It is to be understood that the aspects and objects of the present invention described above may be combinable and that other advantages and aspects of the present invention will become apparent upon reading the following description of the drawings and detailed description of the invention.

BRIEF DESCRIPTION OF THE DRAWINGS

The invention is explained below with the aid of exemplary embodiments with reference to the drawings, which show.

DETAILED DESCRIPTION OF THE PRESENT INVENTION

Figure 1:
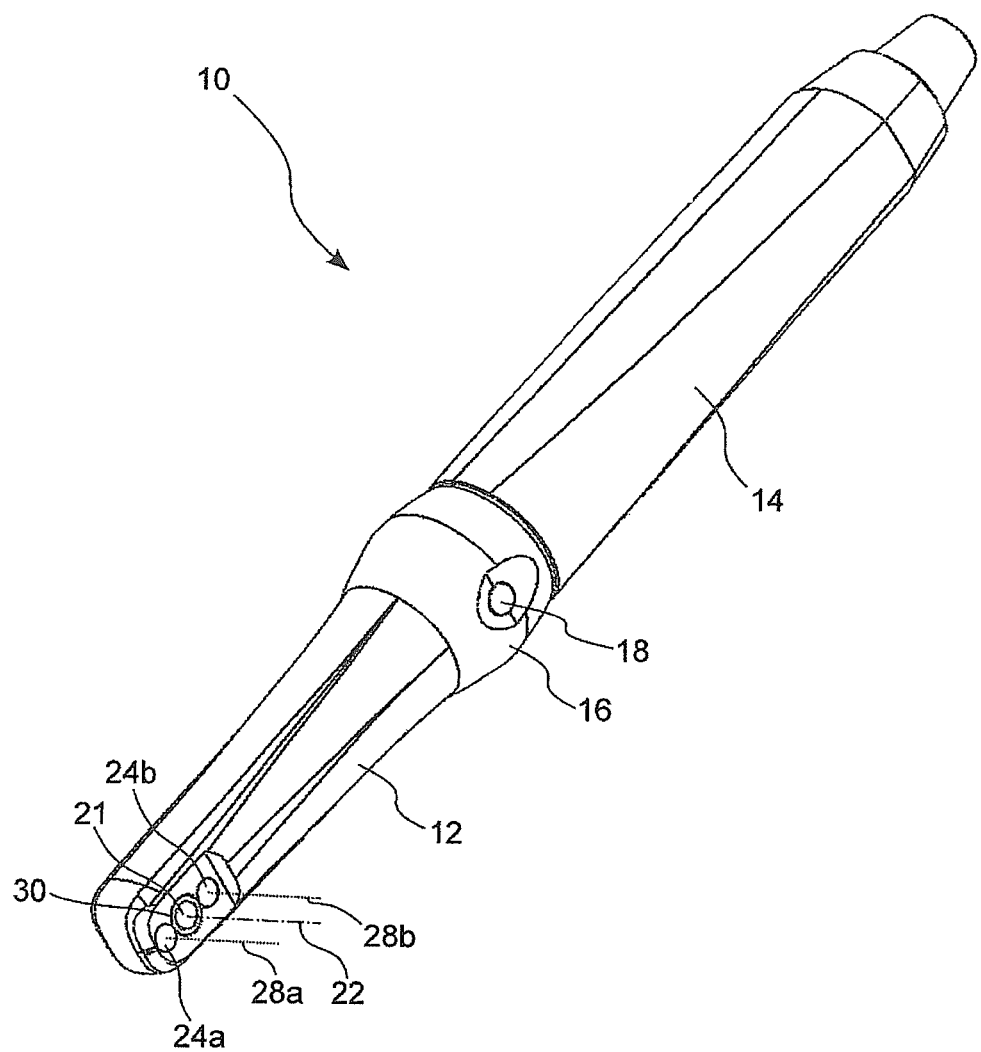
FIG. 1 a perspective view of a dental camera which comprises a camera head for detecting caries in an interdental space.

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

FIG. 1 shows a dental camera 10 with a camera head 12 and a base portion 14. The base portion 14 comprises a grip portion 16 on which two actuating switches 18 and 19 (cf. FIG. 3) are arranged.

Figure 2:
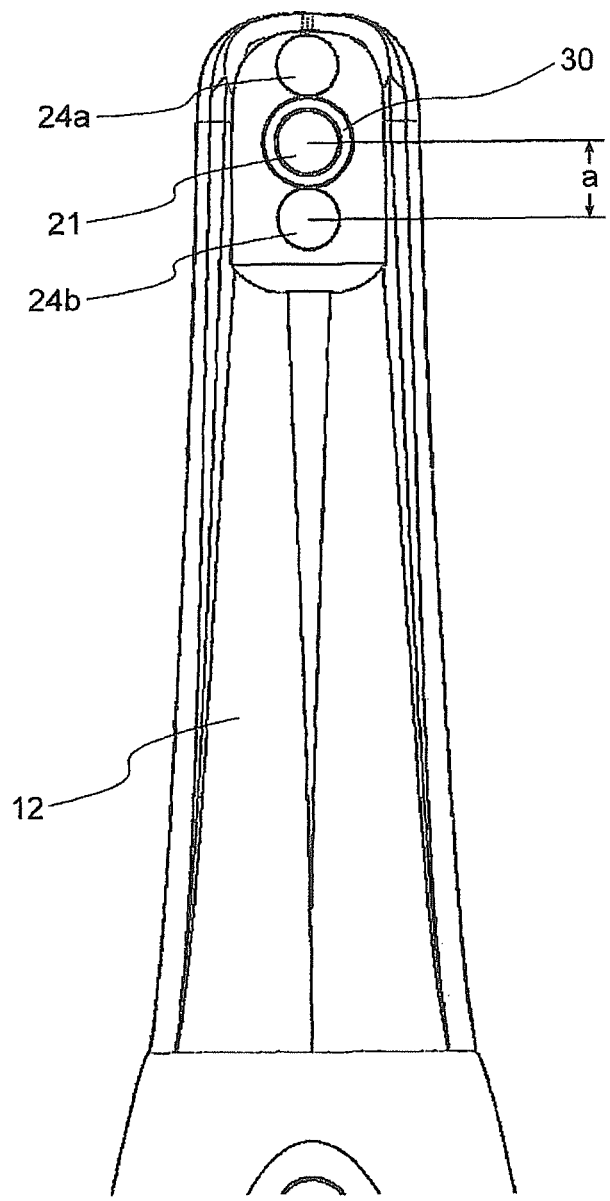
FIG. 2 a plan view of the camera head of the dental camera from below.
Figure 4:
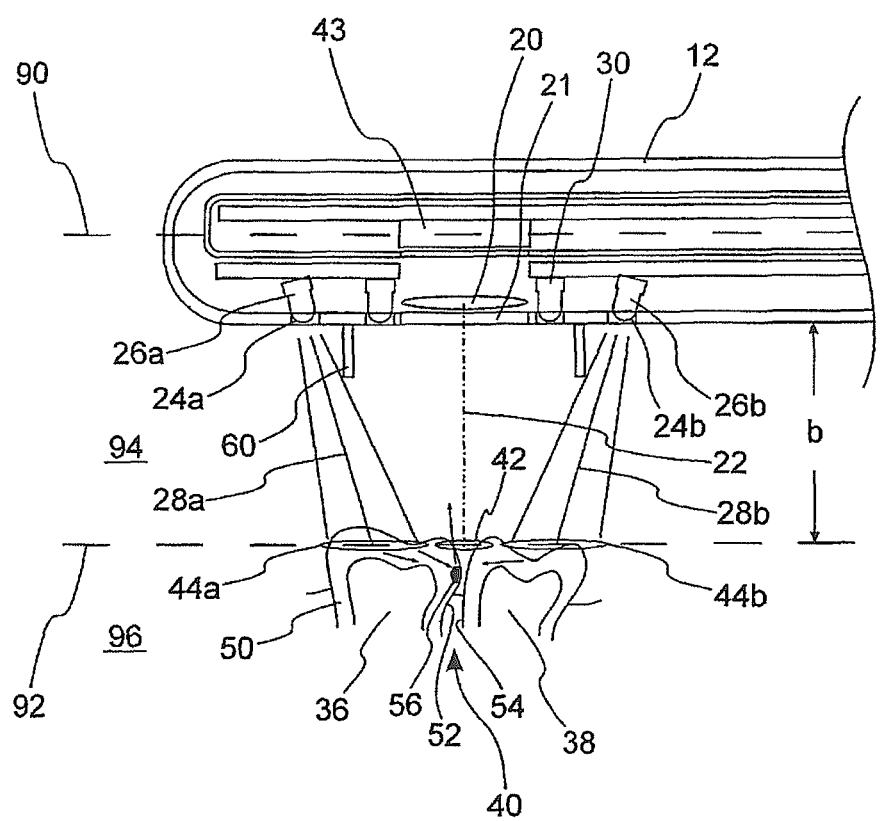
FIG. 4 a side view of the dental camera shown in FIG. 3 and the teeth adjacent to the captured interdental space.

As can be seen more clearly in FIGS. 2 and 4, the camera head 12 has optics 20, shown as lenses, with an entrance window 21 which is arranged near to the distal end of the camera head 12 and whereof the optical axis 22 is shown by a dot and dash line in FIG. 1. In FIG. 4, a broken line moreover shows an image plane 90 in which an image sensor 43 of the dental camera 10 is located, and an object plane 92 which is conjugate therewith. The object plane 92 divides the space into a front half space 94 and a rear half space 96, as seen from the optics 20.

Light exit windows 24a, 24b of an illuminating device are arranged diametrically opposed on both sides of the entrance window 21 in the longitudinal direction of the camera head 12. Infrared light, which is generated by IR LEDs 26a, 26b arranged behind the light exit windows 24a, 24b, exits through these light exit windows 24a, 24b which are shown as circular windows in FIG. 2. The main emission direction 28a, 28b of the infrared light radiated by the illuminating device is indicated by a dotted line in FIG. 1.

As a further illuminating device, the camera head 12 furthermore comprises a white light source 30, which is constructed as a ring extending around the entrance window 21 of the optics 20.

The spacing a between the centre of the entrance window 21 of the optics 20 and the centre of the light exit windows 24a, 24b is 4 mm in the exemplary embodiment shown here, which corresponds approximately to half a tooth diameter of the back teeth along the dental arch.

Figure 3:
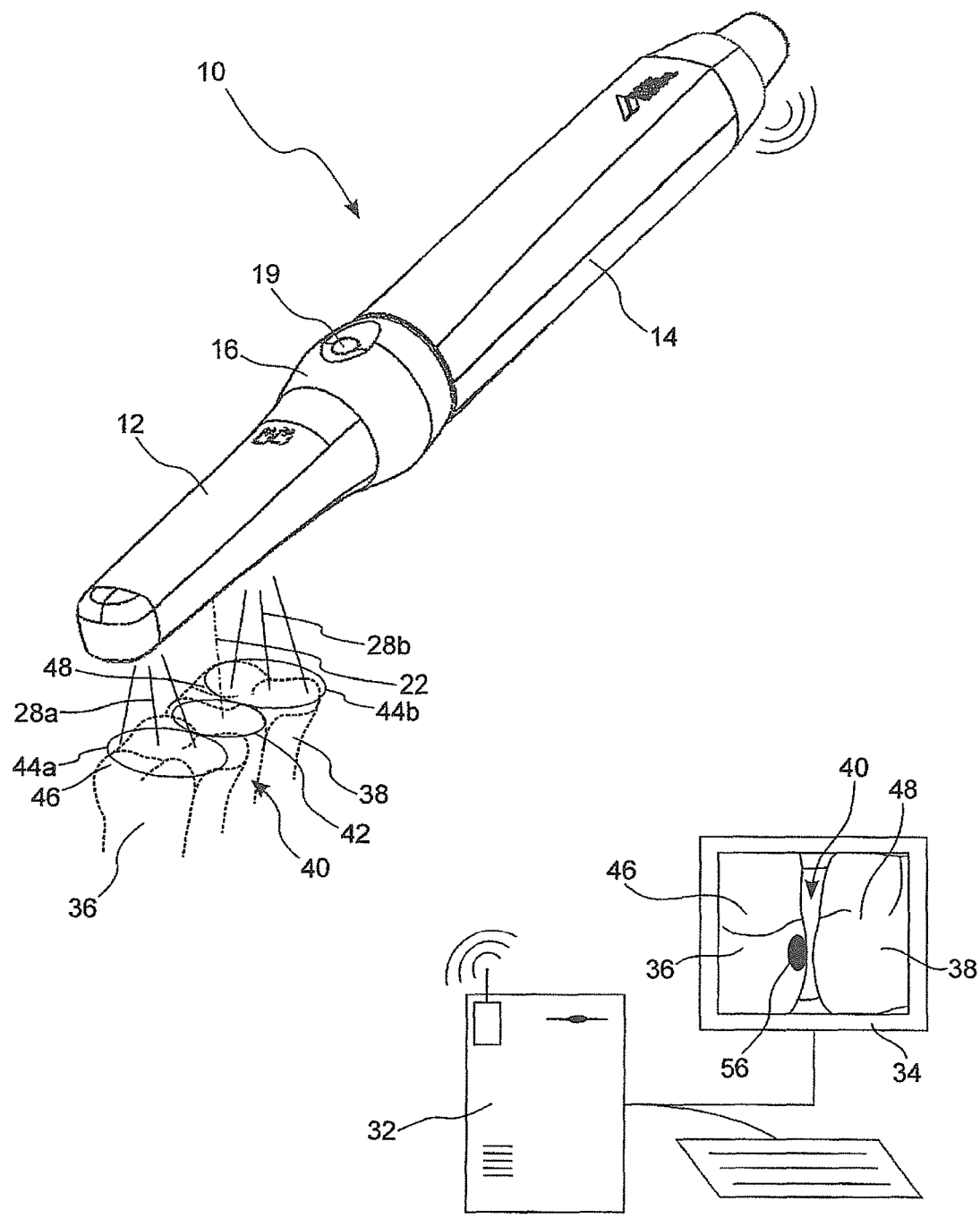
FIG. 3 a perspective view of the dental camera arranged above an interdental space, and a schematic illustration of an associated evaluating unit.

As shown in FIG. 3, the dental camera 10, which is of a wireless construction, communicates by radio (for example by WLAN) with an evaluating unit 32 which can display the result of caries detection on a display device 34 and can store this result for documenting treatment.

The dental camera 10 functions as follows:

As indicated schematically in FIGS. 3 and 4, the camera head 12 is arranged above (or—on the upper dental arch—below) an interdental space 40 located between two adjacent teeth 36 and 38 in such a way that an object field 42 of the optics 20, i.e. the region which is captured thereby and imaged onto an image sensor 43 located in the image plane 90, is directed at the interdental space 40. The camera head 12 is furthermore rotated about the optical axis 22 so that the infrared light exiting the illuminating device in the direction of the rear half space 96 generates infrared light spots 44a, 44b which hit the two occlusal surfaces 46 and 48 of the teeth 36 and 38.

The illuminating device, i.e. in particular the radiation angle and alignment of the IR LEDs 26a, 26b, and the size of the light exit window 24a, 24b are selected here such that, with an operating distance b between the camera head 12 and the occlusal surfaces 46, 48, the infrared light spots 44a, 44b are only of such a size and in such a position that the object field 24 is not illuminated directly by infrared light. This can be additionally ensured by way of a strip 60 (shown only in FIG. 4) which acts as a light barrier and extends around the entrance window 21 and the white light source 30.

With regard to the operating distance b, it should furthermore be pointed out that FIGS. 3 and 4 show a relatively large operating distance b for improved clarity. With a real camera head 12, the operating distance b is selected to be considerably smaller by comparison. The camera head 12 is preferably designed so that it can lie directly against the occlusal surfaces 46, 48 as the photograph is taken.

The dental enamel 50 of the teeth 36, 38 is transparent to the selected infrared light and is therefore transilluminated during illumination by the infrared light. The tooth enamel 50 acts as a type of light guide here, so that the infrared light, as indicated by arrows in FIG. 4, is guided to the interdental space 40 in both teeth 36, 38. If a region 56 which is affected by dental caries is now present on one of the approximal surfaces 52 and 54 of the two teeth 36, 38, the infrared light is scatted thereon, inter alia in the direction of the entrance window 21 of the optics 20, so that it can be captured by the image sensor 43. The affected region 56 therefore appears as a bright spot in a photograph of the interdental space 40.

To draw the attention of the operator to the affected region 56 in suitable manner, the IR LEDs 26a, 26b and the white light source 30 are activated alternately so that the image sensor 43 of the dental camera 10 can capture both an image of the interdental space 40 with visible light as well as a caries attack which can be identified by way of the infrared light. The affected region 56 is then overlaid with the visible image and shown for example by way of a false colour representation on the display device 34.

By way of the actuating switches 18 and 19 on the grip portion 16 of the dental camera 10, the operator can activate a still image function or select whether both teeth 36 and 38 or only one of the two is illuminated by infrared light. The operator can therefore specifically examine the corresponding approximal surfaces 52, 54 of the teeth 36, 38.

Figure 5:
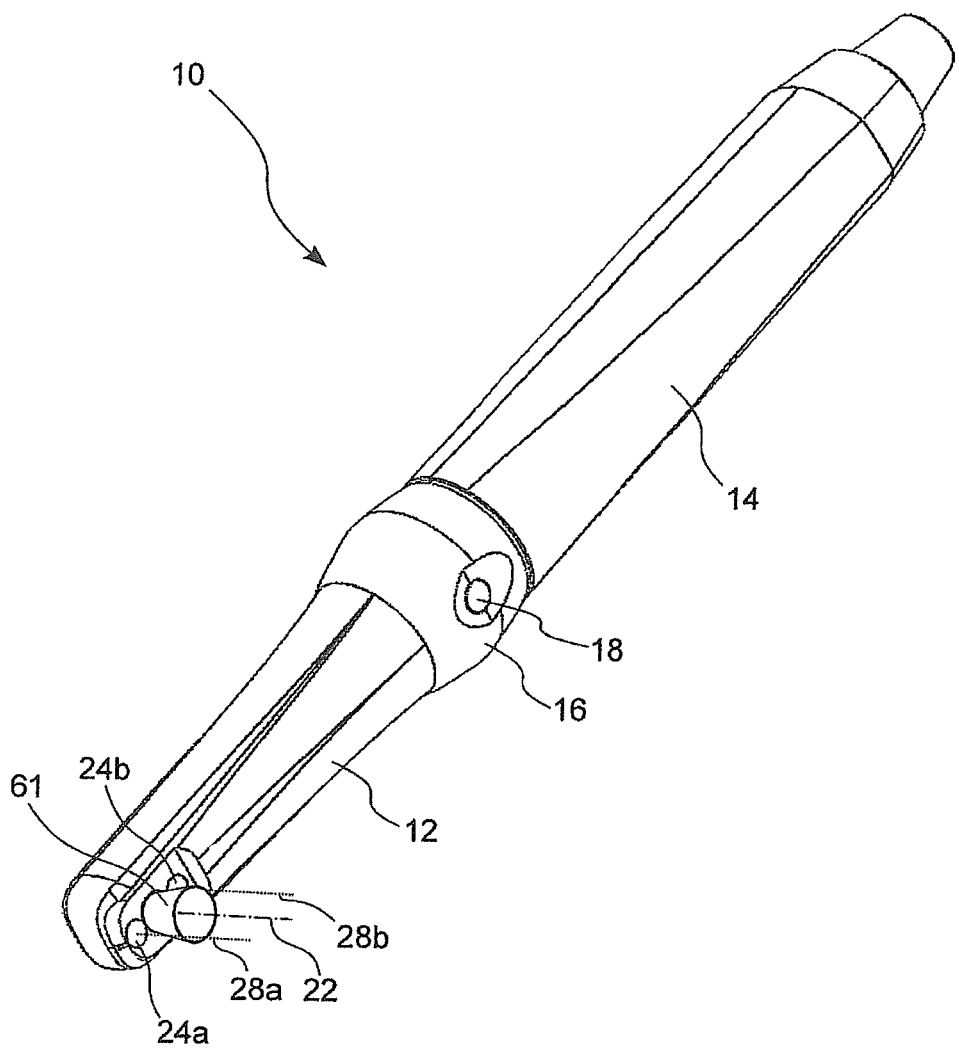
FIG. 5 a dental camera with a light-protection cap.

FIG. 5 shows a dental camera 10 according to a further exemplary embodiment, in which a substantially cylindrical or slightly conically shaped light-protection cap 61 is arranged in front of the entrance window 21 of the optics 20 as a light barrier, which projects transversally in the direction of the optical axis 22. The diameter of the light-protection cap 61 on its camera-side end is selected so that the further illuminating device with the white light source 30 is arranged in the interior of the light-protection cap 61. The light-protection cap 61 serves on the one hand to shield the object field 42 of the optics 20 virtually completely against direct illumination by infrared light. On the other hand, the light-protection cap 61 also shields the object field 42 against incidental environmental light during caries detection.

Figure 6:
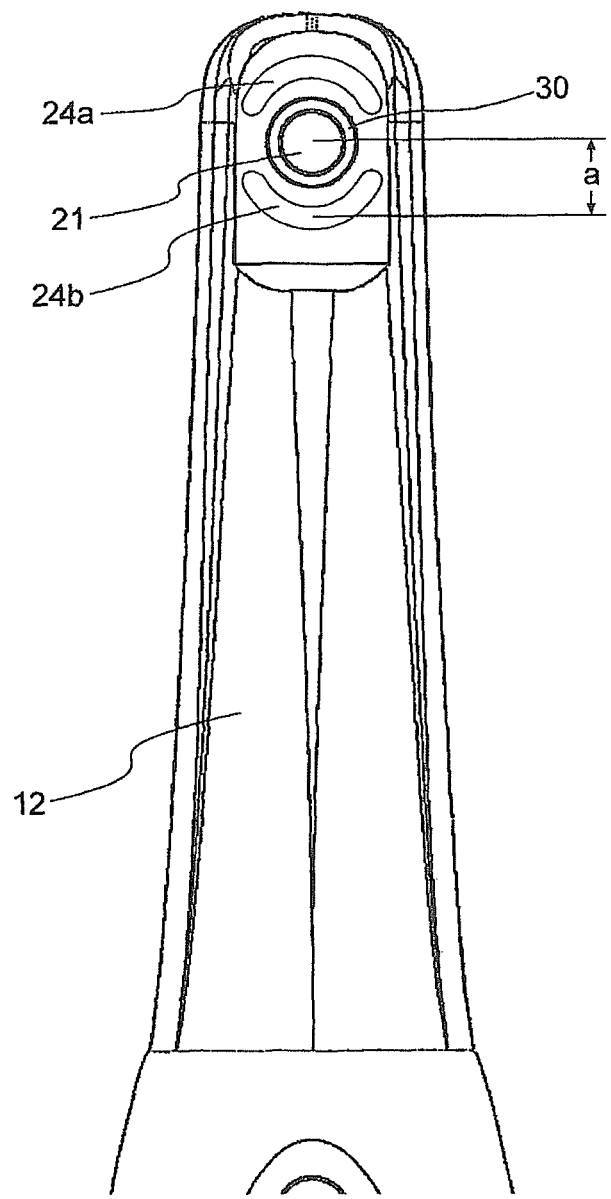
FIG. 6 a plan view of the camera head from below according to an exemplary embodiment with a modified illuminating device.

FIG. 6 shows a camera head 12 according to a further exemplary embodiment, in which the light exit windows 24a, 24b at least partially surround the entrance window 21 of the optics 20 in an arc shape. This camera head 12 enables more comfortable positioning of the camera at different points along the dental arch. This is because the two teeth 36, 38 are illuminated by infrared light over a greater angular range about the optical axis 22, so that the camera head 12 can be handled more flexibly in terms of its rotation about the optical axis 22.

Figure 7:
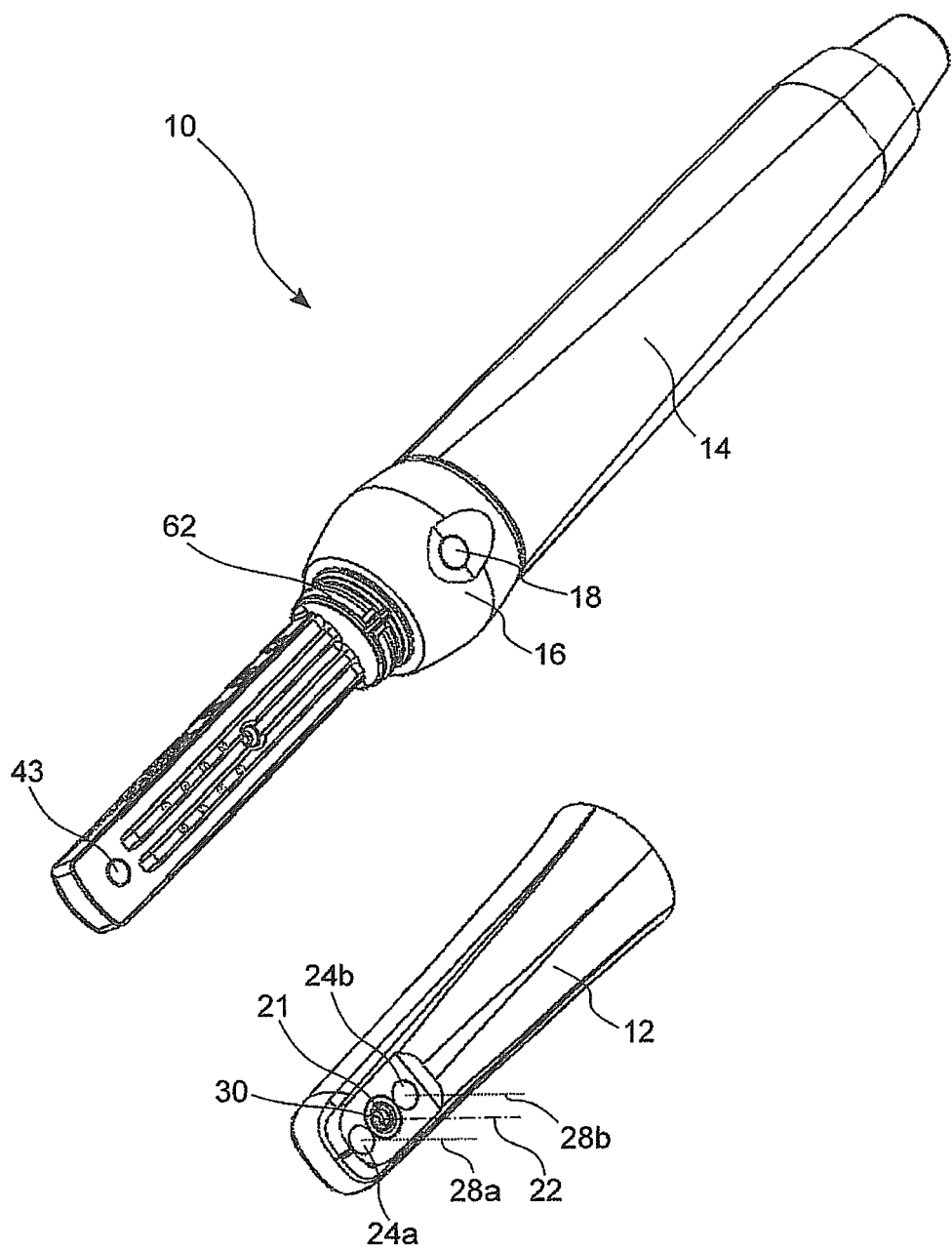
FIG. 7 a perspective illustration of a dental camera in which the camera head is designed as a removable tip and is shown in the unmounted state.

As shown in FIG. 7, the dental camera 10 can be constructed in two parts according to one exemplary embodiment. Depending on the treatment situation, a dental camera 10 of this type enables different camera heads 12 with different functions to be used on a common base portion 14. The base portion 14 here comprises all the necessary components for the basic function of the dental camera 10, such as control electronics including the power supply and the communication means for connection to the evaluating unit 32 and the image sensor 43. The camera head 12, which is constructed as a removable tip in this case, is then connected by way of a latching connection 62 to the base portion 14 in that it is simply pushed thereon and, to detect caries on the approximal surfaces 52, 54, essentially comprises the illuminating device described above for illuminating the teeth 36, 38 with infrared light as well as the associated optics 20.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

The invention claimed is:

1. A dental camera configured to detect caries in an interdental space, the dental camera comprising:
 a base portion;
 a dental camera head removably attached to the base portion, the dental camera head being a transilluminating camera head which is configured to detect caries in an interdental space and comprising
  a housing,
  an image sensor,
  optics positioned adjacent an optics entrance window, the having an image plane and an object plane which are substantially parallel to each other, wherein
   the object plane divides a space into two half spaces, wherein a first half space contains the optics and is located in front of the object plane as seen from the optics and a second half space is located behind the object plane as seen from the optics, and wherein
   the optics are configured to image infrared light on the image sensor located in the image plane,
  an illuminating device,
  two further illuminating devices arranged diametrically opposed in relation to the entrance window of the optics, each illuminating device being positioned linearly with an infrared light source and the entrance window of the optics between the infrared light source and the entrance window of the optics, and
  at least one light barrier, the at least one light barrier having at least a portion positioned linearly with at least one infrared light source, at least one further light source and the entrance window of the optics between the at least one infrared light source and the at least one further light source;

a grip portion and at least two actuating switches configured on the grip portion, wherein the illuminating device comprises two infrared light sources which are arranged diametrically opposed in relation to an entrance window of the optics and the at least two actuating switches can be used to capture still images using the dental camera, and select whether one or both of the two infrared light sources are illuminated, and wherein the illuminating devices and the optics are designed and arranged with respect to one another in such a way that the illuminating device is arranged in the first half space and infrared light exiting the illuminating device is aimed in the direction of the second half space.

2. The dental camera according to claim 1, wherein the infrared light exiting at least one infrared source in the illuminating device has a main emission direction which is parallel to an optical axis of the optics or extends at an angle thereto which is less than 45°, preferably less than 15°.

3. The dental camera according to claim 1, wherein the optics have an optical axis and image an object field, which can be directed at the interdental space and is located in the object plane, onto the image sensor, and in that the illuminating device does not illuminate the object field or at least a cohesive sub-region of the object field which contains the optical axis.

4. The dental camera according to claim 2, wherein the optics have an optical axis and image an object field, which can be directed at the interdental space and is located in the object plane, onto the image sensor, and in that the illuminating device does not illuminate the object field or at least a cohesive sub-region of the object field which contains the optical axis.

5. The dental camera according to claim 1, wherein the illuminating device has a light exit window.

6. The dental camera according to claim 5, wherein the light exit window of the illuminating device is at a spacing from an entrance window of the optics, wherein the spacing is preferably ca. 2 mm to ca. 5 mm, in particular ca. 4 mm.

7. The dental camera according to claim 5, wherein the light exit window extends arcuately, in particular completely annularly, around an entrance window of the optics.

8. The dental camera according to claim 6, wherein the light exit window extends arcuately, in particular completely annularly, around an entrance window of the optics.

9. The dental camera according to claim 5, wherein a light barrier is arranged between the light exit window of the illuminating device and an entrance window of the optics.

10. The dental camera according to claim 9, wherein the light barrier is constructed as a light barrier sleeve which can be connected and released from the dental camera head without tools.

11. The dental camera according to claim 1, wherein at least one of the two infrared light sources is configured to generate infrared light with a middle wavelength which is between ca. 760 nm and ca. 1000 nm, preferably between ca. 820 nm and 890 nm, in particular ca. 850 nm.

12. The dental camera according to claim 1, wherein the two further illuminating light sources each comprise a white light source and are designed to illuminate the interdental space, and in that the optics are permeable both to visible light and to the infrared light of the infrared light source.

13. The dental camera according to claim 1, wherein the dental camera head is constructed as a removable tip and a latching connection removably attaches the dental camera head to the base portion.

14. The dental camera according to claim 1, wherein the image sensor is arranged on the base portion.

* * * * *